United States Patent [19]

Bradshaw et al.

[11] 4,324,792

[45] Apr. 13, 1982

[54] ANTIHISTAMINIC IMIDAZOLES

[75] Inventors: John Bradshaw, Ware; Alexander W. Oxford, Royston; David I. C. Scopes, Ware, all of England

[73] Assignee: Glaxo Group Limited, London, England

[21] Appl. No.: 193,846

[22] Filed: Oct. 3, 1980

[30] Foreign Application Priority Data

Oct. 3, 1979 [GB] United Kingdom ............... 34347/79

[51] Int. Cl.³ .................. A61K 31/445; C07D 233/64
[52] U.S. Cl. .................................. 424/267; 424/248.4; 424/248.54; 424/248.57; 424/248.58; 424/272; 424/273 R; 542/470; 544/63; 544/96; 544/139; 546/210; 548/215; 548/336; 548/342; 548/343; 564/246; 564/276
[58] Field of Search ............... 542/470; 548/336, 342, 548/215; 544/139, 63, 96; 546/210; 424/273 R, 248.54, 248.57, 248.58, 248.4, 267, 272

[56] References Cited

U.S. PATENT DOCUMENTS 2,532,547 12/1950 Goldberg et al. .................. 548/342
3,953,460 4/1976 Durant et al. .................. 548/336 X
4,152,443 5/1979 Durant et al. .................. 548/336 X

OTHER PUBLICATIONS

Labelle, A., et al., *J. Pharm. Exp. Ther.*, 113, 72–88, (1955).
Merck Index, Ninth Edition, p. 279.

*Primary Examiner*—Richard A. Schwartz
*Attorney, Agent, or Firm*—Bacon & Thomas

[57] ABSTRACT

The present invention provides compounds of the general formula (I)

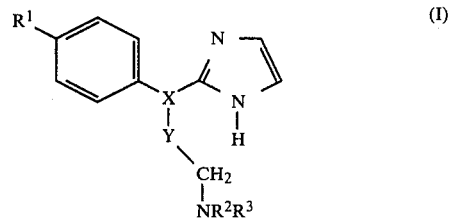

and physiologically acceptable salts and bioprecursors thereof in which

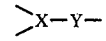

represents either

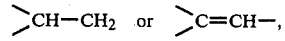

$R^1$ represents hydrogen, halogen, $C_{1-4}$alkoxy, hydroxy, alkyl, $R^4CH(OH)—$, cyano or $R^5CONH—$, $R^2$ and $R^3$, which may be the same or different, each represents a straight or branched chain alkyl group or alkenyl group or $R^2$ and $R^3$ may, together with the nitrogen atom to which they are attached, form a saturated heterocyclic ring containing from 5 to 7 members which may optionally contain an oxygen atom; $R^4$ represents hydrogen or alkyl; and $R^5$ represents hydrogen, alkyl or $C_{1-4}$alkoxy. The compounds have been shown to exhibit $H_1$-antagonist activity in standard pharmacological tests.

11 Claims, No Drawings

ANTIHISTAMINIC IMIDAZOLES

This invention relates to heterocyclic compounds having action on histamine receptors, to processes for their production and to pharmaceutical compositions containing them.

Classical anti-histamines ($H_1$-antagonists) are used for the treatment of conditions in which histamine is a mediator, for example in the treatment of skin afflictions, hay fever and asthma. Compounds of this type suffer from the disadvantage that they produce a significant level of side-effects in man. These often result from the interaction of the anti-histamine with the central nervous system (CNS) of the patient, for example to produce mild to moderate sedation. Other side effects of classical antihistamines are due to their anticholinergic activity, for example dry mouth.

Certain heterocyclic compounds have now been found which exhibit $H_1$-antagonist activity with only weak anti-cholinergic activity. Some of the compounds according to the invention may have advantages over existing anti-histamines that act on $H_1$-receptors in that they are much less lipophilic. This should inhibit penetration of the CNS so that these compounds may have fewer side-effects, especially the sedation usually associated with this type of drug. The compounds according to the invention are of value in the treatment of conditions where anti-histamines that act on $H_1$-receptors are indicated, for example skin afflictions, hay fever and asthma.

The present invention provides compounds of the general formula (I)

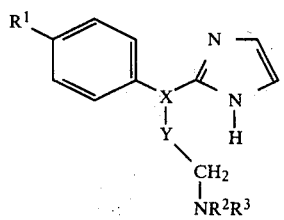

(I)

and physiologically acceptable salts and bioprecursors thereof in which

represents either

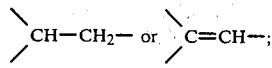

$R^1$ represents hydrogen, halogen, $C_{1-4}$alkoxy, hydroxy, alkyl, $R^4CH(OH)$—, cyano or $R^5 CONH$—; $R^2$ and $R^3$, which may be the same or different, each represents an alkyl group or alkenyl group or $R^2$ and $R^3$ may, together with the nitrogen atom to which they are attached, form a saturated heterocyclic ring containing from 5 to 7 members which may optionally contain an oxygen atom; $R^4$ represents hydrogen or alkyl; and $R^5$ represents hydrogen, alkyl or $C_{1-4}$ alkoxy.

The term "alkyl" as a group or part of a group unless otherwise stated, means that the group is straight or branched and has preferably 1 to 4 carbon atoms, e.g. methyl or ethyl. The term "alkenyl" means that the group is straight or branched and has preferably from 3 to 6 carbon atoms. The term halogen preferably means chlorine or bromine.

The invention includes all optical and geometrical isomers of the compounds of general formula (I) and mixtures thereof.

Geometrical isomers exist where

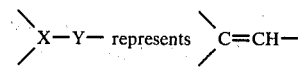

represented in conventional manner as follows:

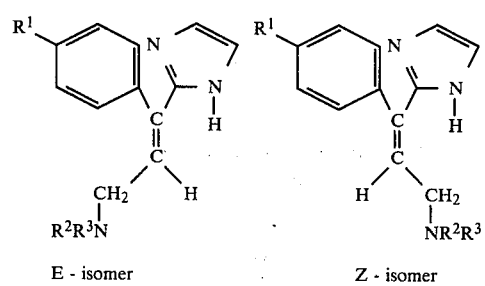

E - isomer  Z - isomer

The invention includes the compounds of general formula (I) in the form of physiologically acceptable salts with inorganic and organic acids. Particularly useful salts include hydrochlorides, sulphates and maleates.

Compounds of the general formula (I), optionally in salt form have been shown to exhibit $H_1$-antagonist activity in standard pharmacological tests. For example they inhibit the contraction of the guinea pig isolated ileum preparation induced by histamine. Certain representative compounds have also been shown to inhibit the action of histamine in the conscious guinea pig using the test described by Loew, Kaiser and Moore, J. Pharmac exp. Ther, 83, 120 (1945).

The compounds according to the invention, optionally in the form of a salt, may be formulated for administration in any convenient way and the invention includes within its scope pharmaceutical compositions containing at least one compound according to the invention adapted for use in human or veterinary medicine. Such compositions may be formulated in a conventional manner using one or more pharmaceutically acceptable carriers or excipients. Formulations for administration of the compounds according to the invention include forms suitable for oral administration, suppositories, injections and forms suitable for administration by inhalation. Oral administration is preferred. For oral administration the pharmaceutical composition may take the form of, for example, tablets, capsules, powders, solutions, syrups or suspensions prepared by conventional means with acceptable excipients. For internal administration, the dosage at which the active ingredient is administered may vary within a wide range, depending on age, weight and condition of the patient. A suitable dose is in the range 4 to 200 mg, taken 1 to 4 times daily.

Preferred meanings for the group $R^1$ are a hydrogen atom, a halogen atom or a methyl, methoxy, hydroxymethyl or 1-hydroxyethyl group and for $R^2$ and $R^3$ are both methyl groups or together with the nitrogen atom to which they are attached form a pyrrolidine ring.

When

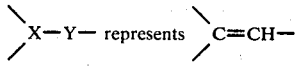

in the general formula (I), the preferred compounds are those in which $R^1$ represents a hydrogen atom or a methyl group and $R^2$ and $R^3$ together with the nitrogen atom to which they are attached form a pyrrolidine ring.

Also, when

then the preferred compounds are the E-isomers.

Preferably the group

represents the group

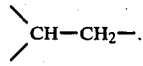

Those compounds of general formula (I) in which

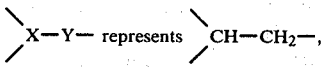

$R^1$ is hydrogen, methoxy, hydroxymethyl or 1-hydroxyethyl and $R^2$ and $R^3$ are both methyl have the additional advantage that they, as determined by the method of Mirrlees et al, J.Med.Chem., 19, 651 (1976), have a low lipophilicity compared with known $H_1$-antagonists which should reduce or minimise CNS side effects. A particularly preferred compound according to the invention is that in which $R^1$ is hydrogen, $R^2$ and $R^3$ are both methyl and

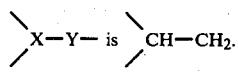

Compounds of general formula (I) in which

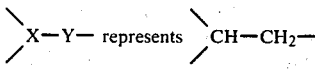

may be prepared from a compound of general formula (II):

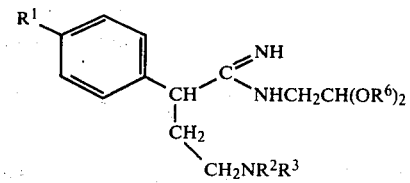

wherein $R^6$ represents a $C_1$-$C_4$ alkyl group (preferably methyl) or the two $R^6$ groups may be linked together to form a cyclic acetal, by treatment with a dilute mineral acid, for example hydrochloric acid, preferably with heating for example to 80° C. to 100° C.

A compound of general formula (II) may be prepared by reaction of an aminoacetaldehyde acetal with an imino ether of general formula (III):

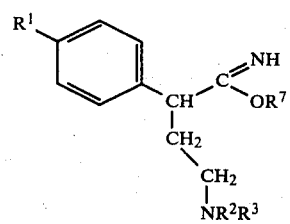

wherein $R^7$ is a $C_1$-$C_6$ alkyl group.

The imino ether of general formula (III) in the form of its hydrochloride salt may be prepared by reaction of a nitrile of general formula (IV)

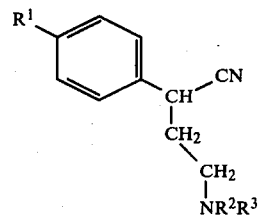

with anhydrous hydrogen chloride and an alkanol, e.g. methanol or ethanol, optionally in the presence of a solvent such as dichloromethane. The imino ether hydrochloride salt can be converted into the free base by reaction with a suitable quantity of an alkoxide, for example sodium alkoxide. The imino ether free base is then reacted with the aminoacetaldehyde acetal generally without isolation to give the compound of general formula (II).

Compounds of formula IV can be prepared by reacting a phenylacetontrile (V)

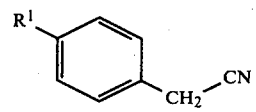

with a compound (VI)

in the presence of a base, for example sodium hydride in a solvent, such as dimethyl formamide, at an elevated temperature, e.g. 50° C.

An alternative method of preparing compounds of general formula (I) wherein

comprises reacting an amidine of general formula (VII)

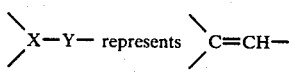 (VII)

with glycollic aldehyde preferably with heating in a solvent such as an alkanol. The amidine (VII) may be prepared from an imino ether (III) by treatment with ammonia in a suitable solvent e.g. methanol. In a modification of this process compounds of formula (I) may be prepared by treating the imino ether (III) with ammonia and glycollic aldehyde in a solvent such as methanol. Preferably the reaction is carried out at elevated temperatures, e.g. 50°–100° C. in an autoclave.

Compounds of general formula (I) in which

may be prepared from a 2-benzoylimidazole of general formula (VIII).

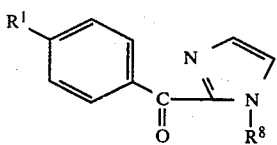 (VIII)

in which $R^8$ is a hydrogen atom or a suitable protecting group, such as ethoxymethyl or benzyl, by reaction with a triphenylphosphonium bromide (IX)

$$R^2R^3NCH_2CH_2\overset{\oplus}{P}Ph_3 \; \overset{\ominus}{Br};$$ (IX)

in the presence of a base to give the compound of formula (X)

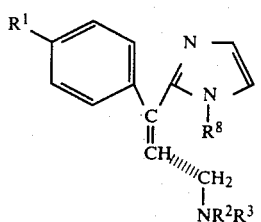 (X)

The reaction may be carried out in a suitable solvent such as tetrahydrofuran in the presence of the base, for example n-butyl lithium, preferably at a temperature of between −30° C. to +20° C.

The protecting group $R^8$ can be removed in conventional manner to give a compound of formula (I) in which

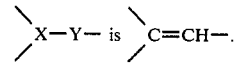

For example, when the protecting group is ethoxymethyl it can be removed by treatment with a mineral acid such as hydrochloric acid. The product represented by formula (X) is a mixture of E and Z isomers which are separable, for example, by preparative layer chromatography.

The ketones (VIII) where $R^8$ is hydrogen are either known compounds or may be prepared by acylation of imidazoles by the method of Bastiaansen and Godefroi, Synthesis, (1978) page 675. The ketones (VIII) where $R^8$ is for example an ethoxymethyl or benzyl group may also be known compounds or may be prepared from 1-substituted imidazoles by the general procedure of Regel and Buchel, (Ann. 159 (1977) 145).

Triphenylphosphonium bromides (IX) may be prepared by fusing the hydrobromide of triphenylphosphine with the appropriate dialkylamino ethanol. Alternatively these compounds can be prepared by heating 2-phenoxyethyltriphenylphosphonium bromide with the appropriate secondary amine in an inert solvent such as dimethylsulphoxide.

Compounds of general formula (I) in which

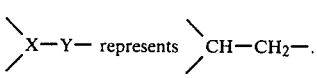

can be also prepared by reducing either isomer of compounds of general formula (I) in which $$\diagdown\!\!\!\!{\phantom{|}}X{-}Y{-}\text{ represents }\diagdown\!\!\!\!{\phantom{|}}C{=}CH{-}.$$

Reduction is effected on either the E- or Z-isomer or on a mixture of the isomers. Reduction can be effected for example by hydrogenation in the presence of a catalyst for example palladium or by treatment with sodium in liquid ammonia, optionally in a solvent such as toluene. Where $R^8$ in the compound of formula (X) is a benzyl group reduction with sodium and liquid ammonia can be carried out directly on the compound of formula (X). The reduction also removes the protecting group and yields the compound of formula (I) in which $$\diagdown\!\!\!\!{\phantom{|}}X{-}Y{-}\text{ represents }\diagdown\!\!\!\!{\phantom{|}}CH{-}CH_2{-}.$$

Compounds of general formula (I) in which $R^1$ represents a hydroxyalkyl group can be prepared from compounds of formula (I) in which $R^1$ represents a group convertible to a hydroxyalkyl group by reduction. Thus for example compounds of general formula (I) in which R¹ represents hydroxymethyl may be prepared by reduction of the corresponding compound of formula (I) in which R¹ is an alkoxycarbonyl group. Reduction may be effected with a suitable metal hydride such as lithium aluminium hydride in a solvent such as tetrahydrofuran or dioxan.

Compounds of general formula (I) in which R¹ represents the group R⁴CH(OH)— may be prepared by reduction of the corresponding compound of formula (I) wherein R¹ represents R⁴CO for example with a metal hydride such as sodium borohydride in a solvent such as ethanol or with hydrogen in the presence of suitable metal catalyst such as platinum. In the latter case if

in the alkanoyl starting compound represents

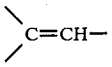

this will also be reduced to

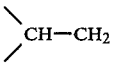

in the resulting compound of general formula (I).

Compounds of formula (I) in which R¹ represents the group R⁵CONH— may be prepared from the corresponding compound of formula (I) in which R¹ represents a primary amino group. For example, compounds in which R⁵ is hydrogen or an alkyl group may be prepared by standard acylation procedures such as reaction with the acid R⁵CO₂H or an activated derivative thereof such as the acid chloride or anhydride.

Compounds of formula (I) in which R¹ represents a cyano group may be prepared from the corresponding compound of formula (I) in which R¹ represents a primary amino group by forming the diazonium salt and reacting this with sodium cyanide.

Compounds of formula (I) in which R¹ is the group —NH₂ may be prepared from compounds of formula (I) in which R¹ is an alkoxycarbonyl group by reaction with hydrazine followed by reaction of the resulting hydrazide with sodium nitrite and hydrochloric acid to give the isocyanate (I;R¹=NCO). This isocyanate is heated with benzylalcohol and the resulting urethane (I:R¹,—NHCO₂CH₂Ph) is hydrogenated in the presence of a metal catalyst such as palladium to give the desired amine (I;R¹,—NH₂).

Compounds of the general formula (I) where R¹ represents the group R⁴CO or an alkoxycarbonyl group may be prepared by the routes described above for preparing the compounds of the invention. For example, compounds where R¹ represents R⁴CO or an alkoxycarbonyl group and the group

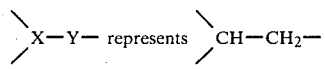

may be prepared from the compound of formula (II) wherein R¹ represents R⁴CO or an alkoxycarbonyl group.

Where the product of any of the above processes is a free base and a salt is required, the salt may be formed in a conventional manner. Thus for example a solution of free base in a suitable solvent, e.g. acetone, may be treated with the appropriate acid.

The invention is illustrated by the following Examples:

EXAMPLE 1

(a)

4-[3-(N,N-Dimethylamino)-1-(imidazol-2-yl)propyl]-benzenemethanol (i) 4-[3-(N,N-Dimethylamino)-1-cyanopropyl]benzoic acid, methyl ester A solution of 4-cyanomethylbenzoic acid, methyl ester (28.8 g) in dry dimethylformamide (DMF) (100 ml) was added dropwise to a stirred suspension of sodium hydride (80%, dispersion in oil, 5.4 g) in DMF (50 ml) under nitrogen. The mixture was stirred at 50° for 1 h., then a solution of dimethylaminoethyl chloride (21.3 g) in DMF (50 ml) was added and stirring was continued at 50° for 18 h.

The mixture was poured onto ice (500 g), acidified and extracted with ethyl acetate (3×200 ml) and the extracts were discarded. The aqueous phase was basified and again extracted with ethyl acetate (3×300 ml). The extracts were dried (Na₂SO₄) and removal of the solvent gave the title compound as a yellow oil, b.p. 146°–150°/0.3 mm (18.8 g).

(a) 4-acetyl-α-(N,N-dimethylaminoethyl)benzeneacetonitrile (3.23 g) was prepared in a similar manner from 4-acetylbenzeneacetonitrile (6.71 g) using tetrahydrofuran in place of DMF as the solvent.

(ii)
4-[3-(N,N-Dimethylamino)-1-(imidazol-2-yl)propyl]-benzoic acid, methyl ester Dry hydrogen chloride was passed into an ice-cooled solution of 4-[3-(N,N-dimethylamino)-1-cyanopropyl]-benzoic acid, methyl ester (5.0 g) and ethanol (5 ml) in dry dichloromethane (100 ml) for 3 h. and the mixture was stirred at room temperature for 18 h. The solution was evaporated to dryness and the residue taken up into dry methanol (50 ml) and treated with sodium methoxide [from sodium 0.48 g, and methanol (20 ml)] and aminoacetaldehyde dimethylacetal (2.2 ml). The mixture was stirred at room temperature for 1 day, then filtered and the filtrate concentrated to a gum. The gum was dissolved in 2 N hydrochloric acid (20 ml), and heated on a steam bath for 2 h. The solution was then basified and extracted with ethyl acetate (3×50 ml). The extracts were dried (Na₂SO₄) and concentrated to a white solid which crystallised from ether/petroleum ether to give the title compound, m.p. 102°–104° (2.3 g). The following compounds were prepared in a similar manner:

(a) 3-(4-chlorophenyl)-3-(imidazol-2-yl)-N,N-dimethyl-1-propanamine m.p. 129°–132° (from ether), τ(CDCl₃)2.7–3.1(4H,m,aromatic,3.1(2H,s,imidazole), 5.87(1H,t,—CH—),7.5–8.2(10 H,s m,CH₂CH₂N(CH₃)₂), from 4-chloro-α-(N,N-dimethylaminoethyl)-benzeneacetonitrile.

(b) N,N-Dimethyl-3-(imidazol-2-yl)-3-phenyl-1-propanamine, m.p. 137°–138° (from ethyl acetate-cyclohexane) (1.64 g), τ(CDCl₃) 2.83(5H,m,aromatic),3.13 (2H,s,imidazole),

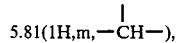
5.81(1H,m,—CH—), 7.6–8.0(8H,m,CH₂—CH₂N(CH₃)₂),7.82(6H,s,N(CH₃)₂) from α-(N,N-dimethylaminoethyl)benzeneacetonitrile (6.0 g).

(c) 1-[4-[3-(N,N-Dimethylamino)-1-(imidazol-2-yl)propyl]phenyl]ethanone m.p. 160°–161° (from ethyl acetate-cyclohexane) (1.65 g) from 4-acetyl-α-(N,N-dimethylamino)benzeneacetonitrile (3.23 g).

(iii) 4-[3-(N,N-Dimethylamino)-1-(imidazol-2-yl)propyl]-benzenemethanol

Lithium aluminum hydride (0.4 g) was added slowly to a stirred solution of 4-[3-(N,N-dimethylamino)-1-(imidazol-2-yl)propyl]benzoic acid, methyl ester (1.0 g) in dry tetrahydrofuran (40 ml) under nitrogen. After stirring for 2 hr., water (3 ml) was added, and the granular suspension was filtered off. The filtrate was evaporated to dryness to give a colourless gum which was dissolved in methanol (5 ml) and treated with a solution of maleic acid (0.4 g) in methanol (5 ml). Solvent was removed and the residual gum was triturated with dry ether to give the maleate salt hemihydrate of the title compound as a glassy, hygroscopic solid, m.p. 65°–66° (1.1 g); τ(D₂O)2.4–2.65(4H,m,aromatic),2.70(2H,s,imidazole),5.33,

5.50(3H,s,HOCH₂,—CH—), 6.7–7.6(10H,m,CH₂CH₂N(CH₃)₂),7.08 (6H,s,N(CH₃)₂).

EXAMPLE 2

N-[4-[1-(Imidazol-2-yl)-3-(N,N-dimethylamino)propyl]phenyl]formamide (i) 4-[3-(N,N-Dimethylamino)-1-(imidazol-2-yl)propyl]-benzoic acid hydrazide A solution of 4-[3-(N,N-dimethylamino)-1-(imidazol-2-yl)propyl]benzoic acid, methyl ester (3.0 g) and hydrazine hydrate (12.5 ml) in ethanol (50 ml) was boiled under reflux for 1 day. Removal of the solvent gave a white solid which was recrystallised from isopropanol-ether to give the title compound, m.p. 168°–170° (2.46 g).

(ii) 3-(4-Aminophenyl)-N,N-dimethyl-3-(imidazol-2-yl)propanamine

A solution of sodium nitrite (0.5 g) in water (5 ml) was added dropwise to a stirred solution of 4-[3-(N,N-dimethylamino)-1-(imidazol-2-yl)propyl]benzoic acid hydrazide (2.0 g) in 2 N hydrochloric acid (10.5 ml) and water (50 ml) at 0° to 5° C. After 30 min. the solution was basified by adding 2 N sodium carbonate (15 ml) and then extracted with ether (3×50 ml). The extracts were dried (Na₂SO₄) and concentrated to an off white solid (1.7 g). This solid was dissolved in toluene (40 ml) and benzyl alcohol (1.5 ml) and heated on a steam bath for 2 h. Solvent was removed and the residue taken up in ethanol (20 ml) and hydrogenated at atmospheric pressure over 10% palladium oxide on charcoal (0.5 g) for 3 h. The catalyst was filtered off and the filtrate treated with a solution of maleic acid (1.8 g) in ethanol (10 ml). Removal of the solvent and trituration of the residue with dry ether afforded a white solid. Recrystallisation from ethanol-ether gave the trimaleate salt of the title compound, m.p. 132°–133° (2.6 g).

(iii) N-[4-[1-(Imidazol-2-yl)-3-(N,N-dimethylamino)propyl]phenyl]formamide

A mixture of 3-(4-aminophenyl)-N,N-dimethyl-3-(imidazol-2-yl)propanamine (0.8 g), formic acid (2 ml) and toluene (50 ml) was boiled under reflux for 2 days in a Dean and Stark apparatus. Solvent was removed and the residue partitioned between 2 N sodium carbonate (25 ml) and ethyl acetate (3×50 ml). The extracts were dried (Na₂SO₄) and concentrated to a white solid. Recrystallisation from ethyl acetate gave the title compound, m.p. 142°–144°, (0.46 g). ν max (CHBr₃) 3445, 3420,3390 (NH), 1690(CO), 1500, 2780 and 2820 cm⁻¹.

EXAMPLE 3

4-[3-(N,N-Dimethylamino)-1-(imidazol-2-yl)propyl]-benzonitrile

A solution of sodium nitrite (0.3 g) in water (5 ml) was added dropwise to a stirred solution of 3-(4-aminophenyl)-N,N-dimethyl-3-(imidazol-2-yl) propanamine (1.0 g) in 2 N hydrochloric acid (6 ml) and water (6 ml), keeping the temperature at 3°–5°. After stirring for 30 min. the dark red solution was adjusted to pH 7–8 and treated with sodium cyanide (0.2 g) and cuprous cyanide (0.4 g) and heated on a steam bath for 3 h. The mixture was then adjusted to pH 11–12 and extracted with ethyl acetate (3×30 ml). The extracts were dried (Na₂SO₄) and concentrated to give the title compound as a gum (0.33 g) which was taken up into methanol (5 ml) and treated with a solution of maleic acid (0.15 g) in methanol (5 ml). Removal of the solvent and trituration of the residue with ether gave the dimaleate salt of the title compound as an off white solid that crystallised from ethanol-ether with m.p. 147°–148°; τ(D₂O)2.06 to 2.35 (2H,m,aromatic),2.48(2H,br.s,imidazole),

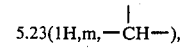
5.23(1H,m,—CH—), 6.5–7.5(4H,m,CH₂CH₂N(CH₃)₂),7.03(6H,s,N(CH₃)₂).

EXAMPLE 4

1-[4-[3-(N,N-Dimethylamino)-1-(imidazol-2-yl)propyl]phenyl]ethanol

A mixture of 1-[4-[(3-N,N-dimethylamino)-1-(imidazol-2-yl)propyl]phenyl]ethanone (1 g) and sodium borohydride (0.1 g) in ethanol (10 ml) and water (1 ml) was stirred at room temperature for 75 h. Additional quantities (0.1 g×2) of sodium borohydride were added after 2.5 h. and 68 h. The mixture was concentrated and the residue partitioned between 2 N sodium carbonate (25 ml) and ethyl acetate (3×25 ml). The extracts were dried (Na$_2$SO$_4$) and evaporated to a yellow gum (0.86 g) which was distilled to give the title compound as a colourless glass b.p. 250°/0.1 mm Hg. (0.65 g) ωmax (CHBr$_3$) 3585(OH), 3440(NH), 2770, 2820(—CH$_2$N(CH$_3$)$_2$).

EXAMPLE 5

N,N-Dimethyl-3-(4-methoxyphenyl)-3-(imidazol-2-yl)propanamine (i)

4-methoxyphenyl-2-(1-phenylmethyl)imidazolyl-methanone

Anisoyl chloride (4.3 ml) was added slowly to a stirred solution of 1-benzylimidazole (5.0 g) in dry acetonitrile (50 ml) keeping the temperature at 25°–30°. After stirring for 1 h. triethylamine (4.4 ml) was added dropwise and the mixture stirred for 18 h. then filtered. The filtrate was concentrated to dryness, and the residue taken up into ether (100 ml) and washed with acetic acid (25%, 3×50 ml), and 2 N sodium carbonate (3×50 ml), then concentrated until the title compound crystallised as a white solid, m.p. 108°–110° (3.1 g).

(ii) (E) and
(Z)-N,N-Dimethyl-3-(4-methoxyphenyl)-3-[(1-phenylmethyl)imidazol-2-yl]-2-propen-1-amine n-Butyl lithium (0.93 M, 11 ml) was added dropwise to a stirred suspension of dimethylaminoethyl triphenylphosphonium bromide (4.1 g) in dry tetrahydrofuran (50 ml) at −30° under nitrogen. The orange solution was allowed to warm to room temperature and a solution of 4-methoxy-phenyl-2-(1-phenylmethyl)imidazolylmethanone (2.9 g) in tetrahydrofuran (20 ml) was added. After stirring for 4 h. hydrochloric acid (2 N, 20 ml) was added and the solvent removed in vacuo. The residual aqueous solution was washed with ethyl acetate (3×50 ml) adjusted to pH9 and then extracted with ethyl acetate (3×50 ml). This solution was extracted with dilute acetic acid (3×50 ml) which was then basified (2 N Na$_2$CO$_3$) and back extracted with ethyl acetate (3×50 ml). The extracts were dried and concentrated and the residue was distilled to give the propenamines as a yellow oil b.p. 250°/0.05 mm Hg (1.36 g) which was used in the next stage.

(iii)
N,N-Dimethyl-3-(4-methoxyphenyl)-3-(imidazol-2-yl)propanamine

A solution of (E) and (Z)-N,N-dimethyl-3-(4-methoxyphenyl)-3-[(1-phenylmethyl)imidazol-2-yl]-2-propen-1-amine (1.0 g) in dry toluene (20 ml) was added to liquid ammonia (20 ml) with stirring at −78°. Sodium was added until the mixture was deep blue (ca. 0.23 g required). After stirring at −78° for 2 h. ammonium chloride (1 g) was added, the mixture allowed to warm to room temperature and the residue partitioned between 2 N sodium carbonate (50 ml) and ethyl acetate (3×50 ml). The organic solution was dried (Na$_2$SO$_4$) and concentrated to give the title compound as a white solid (0.67 g) which crystallised from ether with m.p. 131°–133°, ωmax (CHBr$_3$) 3440 (NH), 2770, 2820 (Me$_2$NCH$_2$—).

EXAMPLE 6

1-(Imidazol-2-yl)-1-(4-methylphenyl)-3-(1-pyrrolidyl)-propane (i)

(1-Ethoxymethylimidazol-2yl)-4-methylphenylmethanone

To a stirred suspension of 1-ethoxymethylimidazole (19.5 g) in dry acetonitrile (300 ml) was added p-toluyl chloride (23.91 g) and triethylamine (15.65 g), keeping the temperature below 35°. The suspension was stirred at room temperature for four days, then the precipitated triethylamine hydrochloride was filtered off and the filtrate concentrated in vacuo. The residue was taken up in ethyl acetate (150 ml) and the organic layer was washed with 2 N sodium carbonate (2×70 ml, 1×50 ml), saturated brine (50 ml) and dried (MgSO$_4$).

Removal of the solvent gave a dark red oil (36 g) which was diluted with ethyl acetate-cyclohexane (15 ml, 1:1) and absorbed onto a column of silica gel (Merck Kieselgel 7736N, 750 g). Elution with ethyl acetate-cyclohexane (1:1) under pressure (60 mm Hg.) afforded an oil contaminated with p-toluic acid. This material was distilled at 0.1 mm.Hg. and the distillate diluted with petroleum ether (4 ml) and filtered to remove the acid. The filtrate was concentrated and distilled to give the title compound as a yellow oil b.p. 180°/0.06 mm (6.89 g).

By the method of Example 6(i) (1-ethoxymethylimidazol-2-yl)-phenylmethanone was prepared from 1-ethoxymethylimidazole and benzoyl chloride.

(ii) (E) and
(Z)-1-[-Ethoxymethylimidazol-2-yl]-1-4-methylphenyl)-3-(1-pyrrolidyl)prop-1-ene A solution of n-butyl lithium in hexane (1.6 M, 7.7 ml) was added dropwise under nitrogen with stirring to a suspension of 2-(1-pyrrolidyl)ethyltriphenylphosphonium bromide (5.41 g) in dry THF (75 ml) keeping the temperature at −10° to −5°. The addition was complete after 5 min. The mixture was then stirred at 0° for 20 min. then cooled to −5° and treated with a solution of (1-ethoxymethylimidazol-2-yl)-4-methylphenylmethanone (3.0 g) in dry THF (30 ml). The mixture was stirred at room temperature for 16 h. and then the precipitated triphenylphosphine oxide was filtered off and washed with a little THF (10 ml). The filtrate and washings were combined and concentrated in vacuo to a yellow syrup. This was absorbed from chloroform (3 ml) onto a column of silica gel (Merck Kieselgel 60, 200 g). Removal of the solvent afforded isomers of the title compound as a thick yellow brown syrup (3.52 g) which was used in the next stage without further purification.

(iii) (E) and
(Z)-1-(imidazol-2-yl)-1-[(4-methyl)phenyl]-3-(1-pyrrolidyl)prop-1-ene A solution of (E) and (Z)-1-[1-ethoxymethylimidazol-2-yl]-1-[(4-methyl)phenyl]-3-(1-pyrrolidyl)prop-1-ene (3.44 g) in ethanol (50 ml), water (50 ml) and conc. hydrochloric acid (3 ml) was heated on a steam bath for 6 days. The mixture was concentrated in vacuo and the residue partitioned between 2 N sodium hydroxide (30 ml) and ethyl acetate (30 ml). The Z-isomer of the title compound crystallised out and was collected and recrystallised from ethyl acetate to give needles, m.p.

193°-5° (dec.) (0.44 g); τ(CDCl₃)—3.7(1H,br.NH), 2.6–3.0(6H,m,aromatic,imidazole)

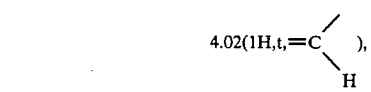

6.8(2H,d,CH₂N),

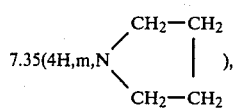

7.68 (3H,s,—CH₃),

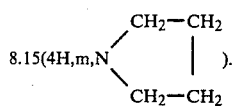

The aqueous layer was extracted again with ethyl acetate (2×30 ml) and the combined extracts were washed with brine (10 ml) and dried (Na₂SO₄). Removal of the solvent gave a sticky pale yellow solid (1.34 g) which was absorbed from dichloromethane (10 ml) onto 7 plates (20×20 cm, Merck alumina 150, F254). Elution with dichloromethane ethanol (30:1) afforded the (E) and (Z)-isomers of the title compound and these were extracted from the stationary phase with ethyl acetate.

A second crop of the Z-isomer had m.p. 191°-194° (dec.) (0.31 g). The E-isomer crystallised from isopropyl acetate with m.p. 151°-2° (dec.) (0.24 g); τ(CDCl₃),1.0 (1H,br,NH),2.72,2.85(4H,m,aromatic), 3.02(2H,s,imidazole),

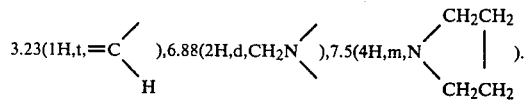

7.62(3H,s,—CH₃),

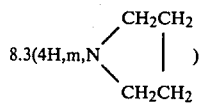

(iv) 1-(Imidazol-2-yl)-1-(4-methylphenyl)-3-(1-pyrrolidyl)-propane

A solution of (Z)-1-(imidazol-2-yl)-1-[(4-methyl)-phenyl]-3-(1-pyrrolidyl)prop-1-ene (0.31 g) in absolute ethanol (40 ml) was hydrogenated over 10% palladium oxide on charcoal (0.03 g). Absorption of hydrogen was complete after 3 h. The catalyst was removed by filtration and the filtrate concentrated to a colourless oil which solidified. Recrystallisation from isopropyl acetate afforded the title compound as pale pink crystals m.p. 125°-127° (0.21 g); τ(CDCl₃)2.92(4H,s,aromatic),3.09(2H,s,imidazole),

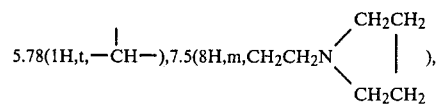

7.68(3H,s,—CH₃),

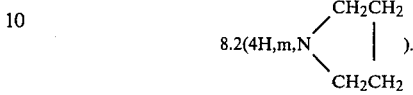

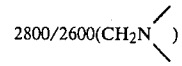

(iv) (a) 1-(Imidazol-2-yl)-1-phenyl-3-(1-pyrrolidyl)-propane (1.71 g) m.p. 131.5-132.5 (from ethyl acetate), νmax (CHBr₃) 3450(NH), 1540(C═N),

2800/2600(CH₂N⟨)

was prepared in a similar manner from a mixture of (Z) and (E)-1-(imidazol-2-yl)-1-phenyl-3-(1-pyrrolidyl)-prop-1-ene(2.0 g).

EXAMPLE 7

N,N-Dimethyl-3-(imidazol-2-yl)-3-phenyl-1-propanamine

Hydrogen chloride was passed into a solution of α-(N,N-dimethylaminoethyl)benzeneacetonitrile (18.8 g) and dry methanol (6.3 ml) in dry dichloromethane (200 ml) for 8 h at 5°-15°. Solvent was removed to give a colourless oil which was taken up in dry methanol (150 ml) and treated with 2 M sodium methoxide solution (65 ml). Aminoacetaldehyde dimethyl acetal (10.6 g) was added and the mixture left to stand overnight. Methanol was then removed and the residue dissolved in 2 N hydrochloric acid (200 ml) and heated at 80° for 30 min. The mixture was cooled, adjusted to pH 9.5 with potassium carbonate and extracted with ethyl acetate (3×200 ml). The extracts were washed with brine (200 ml), concentrated and dried in vacuo to give the title compound, m.p. 135°-136° (16.3 g).

EXAMPLE 8

N,N-Dimethyl-3-(imidazol-2-yl)-3-phenyl-1-propanamine hydrochloride

N,N-Dimethyl-3-(imidazol-2-yl)-3-phenyl-1-propanamine (2.3 g) was stirred with acetone (20 ml) and propan-2-ol (2 ml) and hydrochloric acid (concentrated, 1.0 ml) was added dropwise.

After stirring for 15 min. the product was filtered, washed with acetone (25 ml) and air dried to give the title compound as a monohydrate, m.p. 102°-104° (2.2 g). ωmax.(Nujol) 3500-2200 (—NH⁺), 3500 cm⁻¹ (H₂O).

EXAMPLE 9

N,N-Dimethyl-3-(imidazol)-2-yl)-3-phenyl-1-propanamine

Dry hydrogen chloride was bubbled into a solution of 4-dimethylamino-2-phenylbutyronitrile (1.88 g, 0.01 mol) and dry methanol (0.7 ml) in dichloromethane (20 ml) for 7.5 h. keeping the temperature near to 0°. The solution was then diluted with ether to precipitate the iminoether dihydrochloride as an opaque gum (1.95 g) which was washed with dry ether then taken up into dry methanol (5 ml) and transferred to a 25 ml steel autoclave. Glycollic aldehyde (0.5 g) was added and then liquid ammonia (ca. 15 ml) and the mixture heated at 70°–90° and 15–20 atomspheres for 4.5 h. Ammonia was allowed to evaporate off and the residual solution was diluted with water (50 ml) and extracted with ethyl acetate (50, 4×25 ml). The extracts were washed with water (2×24 ml) and dried ($Na_2SO_4$). Removal of the solvent gave a gum (0.58 g) which was absorbed from ethyl acetate (5 ml) and cyclohexane (5 ml) onto alumina (Merck 90, 30 g). Fractions eluted in cyclohexane-ethyl acetate (4:1, 100 ml) and (1:1, 50 ml) afforded the title compound which crystallised from ethyl acetate (5 ml) and cyclohexane (10 ml) as fine colourless needles, m.p. 132°–134° (0.16 g). The mother liquors afforded a second crop m.p. 130–133 (0.036 g).

EXAMPLE 10

(E)-1-(Imidazol-2-yl)-1-phenyl-3-(1-pyrrolidyl)prop-1-ene

A solution of n-butyl lithium in hexane (1.6 M, 6.5 ml) was added dropwise under nitrogen with stirring to a mixture of 2-(1-pyrrolidyl) ethyltriphenylphosphonium bromide (4.4 g) in dry THF (25 ml) to give a light orange solution of the ylid. After 30 minutes a solution of (1-ethoxymethylimidazol-2-yl)-phenylmethanone (2.3 g) in dry THF (25 ml) was added dropwise. The mixture was allowed to warm to room temperature over one hour and then boiled under reflux for twenty-two hours. The dark brown mixture was cooled, diluted with 2 N hydrochloric acid (12 ml) and water (150 ml) and extracted with ethyl acetate (50, 3×25 ml) then basified with sodium bicarbonate and again extracted with ethyl acetate (5×50 ml). The second extracts were dried ($Na_2SO_4$) and removal of the solvent gave a mixture of the ethoxymethyl derivatives of the isomeric pyrrolidinopropenes as a viscous oil (2.38 g). This was taken up in concentrated hydrochloric acid (80 ml) and aqueous ethanol (1:1, 100 ml) and the solution boiled under reflux for 22 hours, then cooled, diluted with water (50 ml) and extracted with ether (100 ml). The solution was then basified with sodium bicarbonate and extracted with ethyl acetate (2×100 ml, 4×50 ml). The extract was dried ($Na_2SO_4$) and removal of the solvent gave a gum which slowly solidified (1.84 g). This was absorbed from methylene chloride (10 ml) on to six PLC plates (20×20 cm, Merck $Al_2O_3$, F254) and eluted with cyclohexane-ethyl acetate (9:1×1, 1:1×2). The deprotected isomeric propenes separated into two bands which were isolated from the stationary phase by Soxhlet extraction with ethyl acetate. Removal of the solvent gave the Z-isomer as an oil (0.4 g) and the E-isomer (1.1 g) the *title compound,* as an oil which crystallised to a solid m.p. 172°–174° (0.25 g) on trituration with isopropyl acetate. Recrystallisation from isopropyl acetate gave fine needles, m.p. 173–174.5 $\nu$max (CHBr$_3$), 3440(NH), 2800 (CH$_2$ N 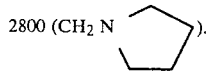 ).

EXAMPLE 11

Pharmaceutical Compositions (a) Tablets

|  | mg/tablet |
|---|---|
| Active ingredient | 50.00 |
| Microcrystalline Cellulose B.P.C. | 149.00 |
| Magnesium Stearate B.P. | 1.00 |
| Compression weight | 200.00 |

The active ingredient is sieved through a 250 μm sieve, blended with the excipients and compressed using 8.5 mm. punches. Tablets of other strengths may be prepared by increasing the compression weight and using punches to suit.

The tablet may be film coated with suitable film forming materials, e.g. methyl cellulose, or hydroxypropylmethyl cellulose, using standard techniques. Alternatively the tablets may be sugar coated.

(b) Capsules

|  | mg/capsule |
|---|---|
| Active ingredient | 50.00 |
| *STA-RX 1500 | 49.50 |
| Magnesium stearate B.P. | 0.50 |

*A form of directly compressible starch.

The active ingredient is sieved through a 250 μm sieve and blended with the other materials. The mix is filled into No3 hard gelatin capsules using a suitable filling machine. Other doses may be prepared by increasing the fill weight and if necessary changing the capsule size to accommodate the increase.

(c) Sustained Release Tablets

|  | mg/tablet |
|---|---|
| Active ingredient | 200.00 |
| +Cutina HR | 50.00 |
| Lactose B.P. | 247.50 |
| Magnesium stearate B.P. | 2.50 |

+Cutina HR is a grade of microfine hydrogenated castor oil.

The active ingredient is sieved through a 250 μm sieve and blended with the Cutina HR and lactose. The mixed powders are moistened with Industrial Methylated Spirits 74 O.P., granules are made, dried, screened and blended with the magnesium stearate. The lubricated granules are compressed using 10.5 mm punches to produce tablets with a hardness of not less than 10 Kp (Schleuniger hardness tester).

(d) Syrup

|  | mg/5ml dose |
|---|---|
| Active ingredient | 50.00 |
| Sucrose B.P. | 2750.00 |
| Glycerine B.P. | 500.00 |
| Buffer | |
| Flavour | |
| Colour | as required |
| Preservative | |
| Distilled water to | 5.0 ml |

The active ingredient, buffer, flavour, colour and preservative are dissolved in some of the water, and the glycerine is added. The remainder of the water is heated to 80° C. and the sucrose is dissolved in this and cooled. The two solutions are combined, adjusted to volume and mixed. The syrup produced is clarified by filtration.

(e) Injection for Intravenous Administration

|  | % w/v |
| --- | --- |
| Active ingredient | 0.50 |
| Water for injections B.P. to | 100.00 |

Sodium chloride may be added to adjust the tonicity of the solution and the pH may be adjusted to that of maximum stability using either dilute acid or alkali.

We claim:

1. A compound of the formula (I)

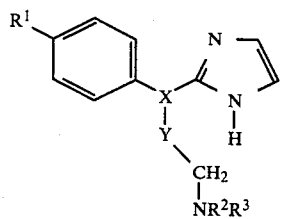

or a physiologically acceptable salt thereof in which

X—Y— represents either CH—CH$_2$ or C=CH—; R$^1$ represents hydrogen, halogen, C$_{1-4}$ alkoxy, hydroxy, C$_{1-4}$ alkyl, R$^4$CH(OH)—, cyano or R$^5$CONH—; R$^2$ and R$^3$, which may be the same or different, each represents a C$_{1-4}$ alkyl group or C$_{3-6}$ alkenyl group or R$^2$ and R$^3$ form a saturated alkylene chain and together with the nitrogen atom to which they are attached form a saturated heterocyclic ring containing from 5 to 7 members;

R$^4$ represents hydrogen or C$_{1-4}$ alkyl; and

R$^5$ represents hydrogen, C$_{1-4}$ alkyl or C$_{1-4}$ alkoxy.

2. The compound according to claim 1 in which

R$^1$ represents a hydrogen atom, a halogen atom, or a methyl, methoxy, hydroxymethyl or 1-hydroxyethyl group and R$^2$ and R$^3$ both represent methyl groups or together with the nitrogen atom to which they are attached form a pyrrolidine ring.

3. The compound according to claim 1 in which

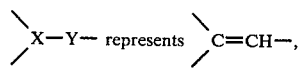

R$^1$ represents a hydrogen atom or a methyl group and R$^2$ and R$^3$ together with the nitrogen atom to which they are attached form a pyrrolidine ring.

4. The compound as claimed in claim 3 in the form of the E-isomer.

5. The compound as claimed in claim 2 in which R$^1$ is hydrogen, methoxy, hydroxymethyl or 1-hydroxyethyl and R$^2$ and R$^3$ are both methyl.

6. The compound claimed in claim 5 which is N,N-dimethyl-3-(imidazol-2-yl)-3-phenyl-1-propanamine or physiologically acceptable salt thereof.

7. The compound of claim 6 in the form of its hydrochloride salt.

8. The compound of claim 1, wherein R$^1$ is chlorine or bromine.

9. A pharmaceutical composition for treatment of a condition mediated through histamine H$_1$ receptors comprising an effective amount to relieve said condition of a compound according to claim 1 and at least one inert pharmaceutically acceptable carrier or diluent.

10. A pharmaceutical composition according to claim 9, in a form suitable for oral administration and containing 4 to 200 mg of the active compound.

11. A method of treating a condition mediated through histamine H$_1$-receptors which comprises administering to a patient an effective amount of a compound according to claim 1 to relieve said condition.

* * * * *